United States Patent

Vanonou

[11] Patent Number: 5,587,168
[45] Date of Patent: Dec. 24, 1996

[54] COSMETIC PREPARATIONS

[76] Inventor: Ilana Vanonou, 3300 NE. 192nd St., Aventura, Fla. 33180

[21] Appl. No.: 243,485

[22] Filed: May 16, 1994

[51] Int. Cl.$^6$ ................................................. A61K 7/46
[52] U.S. Cl. ..................... 424/401; 424/74; 424/195.1; 424/649; 424/618; 512/5; 512/7
[58] Field of Search ..................... 424/649, 401, 424/70, 195.1, 618; 512/5, 7

[56] References Cited

FOREIGN PATENT DOCUMENTS 2554715  11/1983  France .
0390012  4/1991  Japan .

*Primary Examiner*—Jyothsna Venkat
*Attorney, Agent, or Firm*—Beveridge, DeGrandi, Weilacher & Young, L.L.P.

[57] ABSTRACT

The present invention relates to cosmetic preparations containing finely divided, solid particles of gold, silver or platinum.

3 Claims, No Drawings

COSMETIC PREPARATIONS

The present invention relates to novel cosmetic preparations such as perfumes, fragrances, shampoos, rinses, cremes, lotions and any type of cosmetic formulation applied to the human body or any part thereof to obtain the desired cosmetic effect. The cosmetic preparations of this invention contain finely divided, solid particles of metal, preferably gold, silver or platinum and especially yellow gold or white gold.

In one aspect of the invention, a fragrance or perfume formulation contains a perfume, fragrance or aroma chemical, optionally one or more conventional additives typical for such formulations, and as the essential ingredient, a very finely divided metal, particularly yellow gold, white gold, silver or platinum and more preferably yellow gold. The finely divided metal solid particles; e.g. gold, are in the form of flakes, leaves, powder or shavings. When present in a perfume or fragrance of a transparent or translucent nature, the finely divided gold particles will typically be seen to settle to the bottom of the perfume container but when the perfume formulation is shaken, the finely divided metal will float throughout the medium and will eventually settle by gravitational forces. It the medium is of a more viscous nature such as a creme or lotion, the metal powder will remain more suspended throughout the product and will not settle as easily as in a low viscosity or liquid cosmetic product.

It is therefore a feature of the invention to introduce finely divided metal particles, such as gold, into any type of perfume, fragrance, shampoo, hair rinse, body cream, body lotion, spray fragrance, cologne and the like cosmetic preparation.

The gold particles will be clearly visible in a transparent or essentially transparent medium and will create a sense of luxury and opulence in the user. Yet at the same time the metal particles will not be noticeable to any great degree when the product is applied in use.

The size of the metal particles can vary widely but should be extremely finely divided so that when the cosmetic is deposited and dubbed onto the skin, to the unaided eye the particles will disappear or be essentially invisible.

The proportions of the gold or the metal material that is added to the cosmetic formulation is not narrowly critical but is a small amount typically less than 5% by volume and more especially in the range of 0.1 to 0.005% by volume. Larger amounts can be used and is only limited by the need to form a product which will appear desirable in the eyes of the customer. Therefore, the amount of finely divided noble metal material is not critical from the standpoint of operability of the invention but is only limited in terms of economics and what will appear to be most attractive to the ultimate consumer. The quantity of metal; e.g. gold, is such that it will be clearly visible in a transparent or essentially transparent cosmetic base and will become dispersed when the cosmetic preparation is shaken. In cremes and other cosmetics of higher viscosity than perfumes the metal will remain dispersed in the product upon standing. Appropriate known dispersing agents can be used for that purpose.

It is of course possible to include mixtures of metals such as yellow gold and white gold or silver and gold, etc. When using gold, 14K or 24K gold is especially preferred.

The following examples serve to illustrate the invention but are not narrowly limiting thereof.

A fragrance of the following formulation is used in combination with finely divided gold flakes to produce a gold containing fragrance formulations:

EXAMPLE I

| | |
|---|---|
| Orange oil | 6 g |
| Phenylethyl alcohol | 8 g |
| Rosewood oil | 10 g |
| a-Hexylcinnamaldehyde | 10 g |
| Brazyl acetate | 5 g |
| Coumarin | 10 g |
| Heliotropin | 5 g |
| Vanillin | 5 g |
| Isomethyliosome | 12 g |
| Mixture of methyl ketones obtained from treated cedar oil (product marketed under the name "VERTOFIX" and sold by "I.F.F." | 11 g |

50 grams of the above perfume are mixed with 0.5% by volume of extremely finely divided gold shavings to yield a perfume composition according to the invention.

EXAMPLE II

| | |
|---|---|
| Orange oil | 8 g |
| Mandarin oil | 8 g |
| Orange Petitgrain oil | 7 g |
| Linalyl acetate | 12 g |
| a-Hexylcinnamaldehyde | 11 g |
| Patchouli oil | 6 g |
| Musk ketone | 6 g |
| Vetiver oil | 11 g |
| "VERTOFIX" product defined in Example I | 13 g |
| Isomethylionone | 10 g |

To the above is added 0.3% by volume of finely divided 24K gold shavings to form a perfume.

As employed herein and in appended claims the term "perfume" is used in its ordinary sense to refer to and include any essentially water insoluble fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders and stabilizers. These auxiliaries are also included within the meaning of "perfume", as used herein. Typically, perfumes are complex mixtures of a plurality of organic compounds, which may include odoriferous or fragrant essential hydrocarbons, such as terpenes, ethers and other compounds which are of acceptable stabilities in the present compositions. Such materials are either well known in the art or are readily determinable by simple testing, and so need not be listed in detail here.

It has been noted that the best perfumes for this purpose are those which are in the following olfactory families: floral, including floral, green floral, woody floral and fruity floral; chypre, including floral aldehydic chypre, leather chypre and green chypre; fougere; amber, including floral woody amber, floral spicy amber, sweet amber and semi-floral amber; and leather.

Perfume components and mixtures thereof which can be used for the preparation of such perfumes may be natural products such as essential oils, absolutes, resinoids, resins, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Examples of such perfume components are geraniol, geranyl acetate, linalool, linaly acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzylcarbinol, trichloromethylphenylcarbinyl methylphenylcarbinyl acetate, p-tert-butylcyclohexyl acetate, isononyl acetate, vetiveryl acetate, vetiverol, alpha-n-amylcinammic aldehyde, alpha-hexyl-cinammic aldehyde, 2-methyl-3-(p-tert-.butylphenyl)-propanal, 2-methyl-3-(p-isopropyl-phenyl)propanal, 3-(p-tert.butylphenyl)propanal, tricyclodecenyl acetate, tricyclodecenyl propionate, 4-(4-hydroxy-4-methylpentyl)-3-cyclohexenecarbaldehyde, 4-(4-methyl- 3-pentenyl)-3-cyclohexenecarbaldehyde, 4-acetoxy-3pentyltetrahydropyran, methyl dihydrojasmonate, 2-n-heptylcyclopentanone, 3-methyl-2-pentyl-cyclopentanone, n-decanal, n-dodecanal, 9-decenol-1, phenoxyethyl isobutyrate, phenylacetaldehyde dimethyl acetal, phenylacetaldehyde diethyl acetal, geranonitrile, citronellonitrile, cedryl acetal, 3-isocam-phylcyclohexanol, cedryl methyl ether, isolongifolanone, aubepine nitrile, aubepine, heliotropine, coumarin, eugenol, vanillin, diphenyl oxide, hydroxycitronellal ionones, methyl ionones, isomethyl ionomes, irones, cis-3-hexenol and esters thereof, indane musk fragrances, tetralin musk fragrances, isochroman musk fragrances, macrocyclic ketones, macrolactone musk fragrances, ethylene brassylate, aromatic nitro-musk fragrances. Suitable solvents, diluents or carriers for perfumes as mentioned above are for examples; ethanol, isopropanol, diethylene, glycol monoethyl ether, dipropylene glycol, diethyl phthalate, triethyl citrate, etc. Any suitable organic solvent that does snot interact with the fragrance, cosmetic formulation ingredients or the metal particles can be used.

For incorporation into cremes, lotions, shampoos, hair rinses, sun screens and the like, all of which are included herein by the term "cosmetic base" or "cosmetic formulation", any conventional product can be used in accordance with the present invention. All that is necessary is to mix the finely divided metal with the cosmetic formulation.

In another aspect of the invention there is provided a perfumed candle containing finely divided metal particles.

Further variations and modifications of the foregoing will be apparent to those skilled in the art and are intended to be encompassed by the claims appended hereto.

I claim:

1. A cosmetic preparation which is a transparent medium of fragrance or perfume consisting essentially of a fragrant substance selected from the group consisting of a natural extract of flowers, herbs, leaves, roots, barks, wood, blossoms, plants, and mixtures thereof, and 0.1 to less than 5% by volume of finely divided yellow gold; wherein said yellow gold flakes are of a size such that when said cosmetic preparation is applied to the skin said yellow gold flakes will disappear or be essentially invisible to the unaided eye, said yellow gold flakes being visible in said transparent medium and when said cosmetic preparation is shaken said yellow gold flakes will float throughout said transparent medium and eventually settle by gravitational forces.

2. The cosmetic preparation according to claim 1 wherein the flakes are 14K gold.

3. The cosmetic preparation according to claim 1 wherein the flakes are 24K gold.

* * * * *